(12) United States Patent
Chadwick et al.

(10) Patent No.: US 6,276,069 B1
(45) Date of Patent: *Aug. 21, 2001

(54) BRASSIERE SIZER

(75) Inventors: Douglas Owen Chadwick, Kenosha, WI (US); Mala Kathleen Brindisi, Gurnee, IL (US)

(73) Assignee: Jockey International, Inc., Kenosha, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/267,906

(22) Filed: Mar. 1, 1999

(51) Int. Cl.$^7$ ................... G01B 3/10; G06G 3/00
(52) U.S. Cl. .................. 33/512; 33/1 SB; 33/764; 235/78 R
(58) Field of Search .................. 33/1 SB, 2 R, 33/755, 759, 764, 512, 555.1, 555.4; 235/61 A, 61 R, 78 R, 88 R

(56) References Cited

U.S. PATENT DOCUMENTS

| | | | |
|---|---|---|---|
| D. 204,804 | 5/1966 | Gershen | D52/1 |
| D. 271,025 | 10/1983 | Li | D18/2 |
| D. 295,149 | 4/1988 | Markin | D10/70 |
| D. 295,150 | 4/1988 | Farrell | D10/71 |
| D. 299,436 | 1/1989 | Muth | D10/62 |
| D. 348,226 | 6/1994 | Alaniz | D10/61 |
| 2,008,153 | 7/1935 | Payne et al. | 273/148 |
| 2,205,626 | 6/1940 | Mason | 33/179 |
| 2,280,485 * | 4/1942 | Harris | 33/1 SB |
| 2,527,206 | 10/1950 | Amyot | 33/169 |
| 2,559,501 | 7/1951 | Graf | 33/2 |
| 2,575,343 | 11/1951 | Heiman | 33/2 |
| 2,965,292 | 12/1960 | Lewis | 235/78 |
| 2,967,016 | 1/1961 | Gray | 235/61 |
| 3,309,017 | 3/1967 | Koskela | 235/78 |
| 4,164,816 | 8/1979 | Bergkvist | 33/139 |
| 4,178,691 | 12/1979 | Tateishi | 33/139 |
| 4,195,348 | 3/1980 | Kakutani | 364/562 |
| 4,211,011 * | 7/1980 | Jacobson | 33/759 |
| 4,454,409 | 6/1984 | Sehres | 235/78 R |
| 4,506,446 | 3/1985 | Mitchell | 33/139 |
| 4,882,850 | 11/1989 | Lindsey | 33/760 |
| 5,027,526 | 7/1991 | Crane | 33/763 |
| 5,406,715 | 4/1995 | Koizumi et al. | 33/706 |
| 5,414,943 | 5/1995 | Vogt | 33/764 |
| 5,619,804 | 4/1997 | Vogt et al. | 33/763 |

FOREIGN PATENT DOCUMENTS

| | | | |
|---|---|---|---|
| 232703 * | 4/1925 | (GB) | 33/512 |
| 106911 * | 12/1963 | (NL) | 33/512 |

OTHER PUBLICATIONS

VictoriasSecret.com,—Bra Salon; "Measuring for a Perfect Fit" (no date).

* cited by examiner

Primary Examiner—G. Bradley Bennett
(74) Attorney, Agent, or Firm—Michael Best & Friedrich LLP

(57) ABSTRACT

A brassiere sizer includes a housing having a front, side, and rear walls. A first set of indicia is provided on the front wall and comprises length increments equally spaced apart and disposed in a circular array on the side wall and a second indicia is provided on the front wall and comprises brassiere cup size indicia equally spaced apart and in an arcuate array concentric with the first set of indicia. A dial mounted on the first member for rotation about a rotation axis concentric with the first set of indicia, and a third set of indicia is provided on the dial in a spaced apart circular array and denominating length increments and disposed adjacent to the first set of indicia. A window in the dial is positioned to be adjacent to the cup size indicia on the front housing face. First and second measurement tapes are mounted on the housing for sliding movement. The length measurement indicia on the first member corresponds to the length increment on the first tape and the length measurement indicia on the second member corresponds to the length measurement indicia on the second tape.

14 Claims, 2 Drawing Sheets

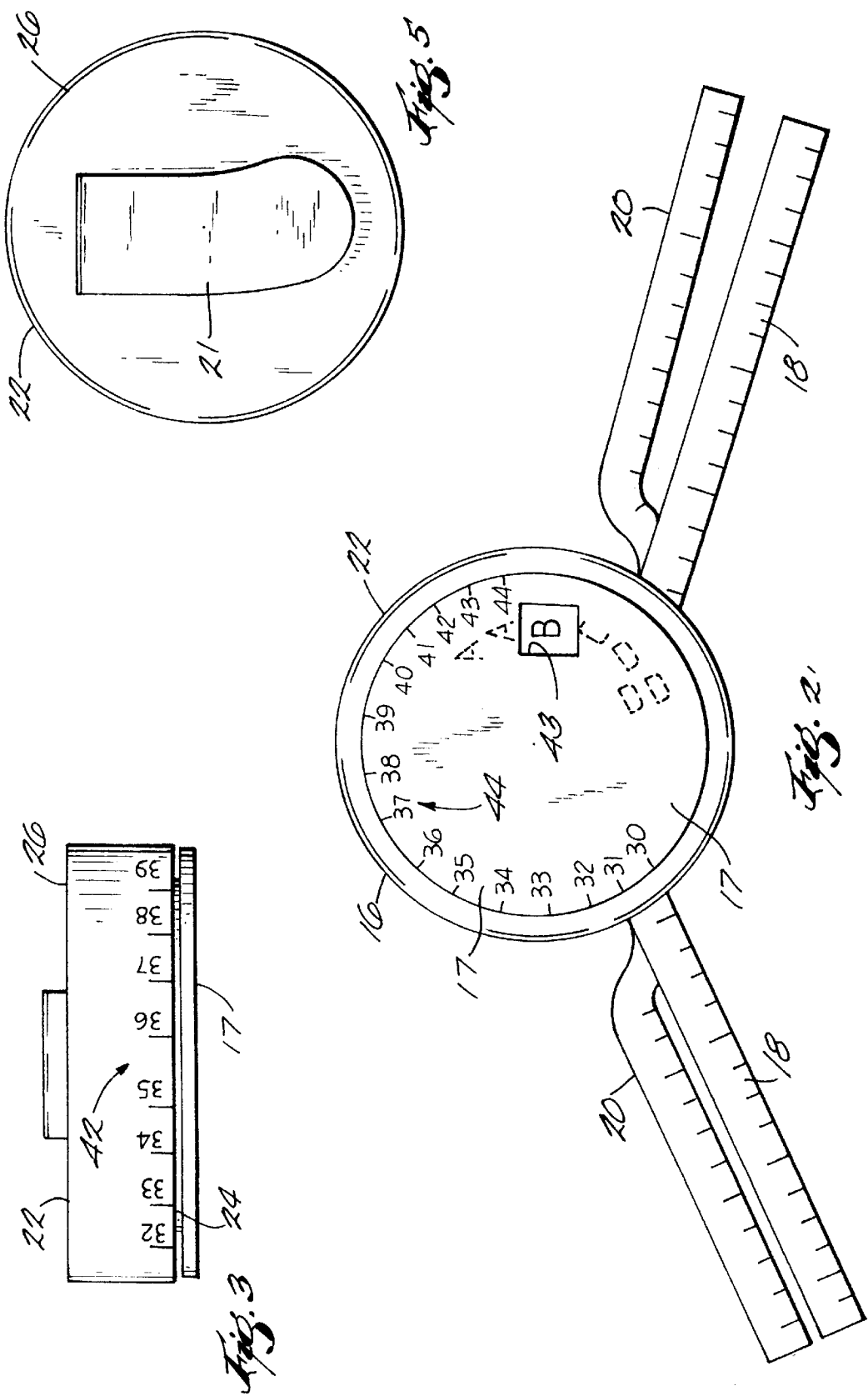

BRASSIERE SIZER

BACKGROUND OF THE INVENTION

This invention relates to measuring and calculating devices and, more particularly, to a brassiere sizer.

Brassiere sizes generally involve two variables. These are band size and cup size. Band size is generally determined by a direct chest measurement to which five inches are normally added. The cup size is normally determined by a comparison of the corrected band measurement to a breast measurement. Brassiere sizes have been determined in the past by several methods. For example, U.S. Pat. No. 4,454,409 discloses a brassiere size calculator which employs measurements made with a separate tape. U.S. Pat. Nos. 5,414,493 and 5,619,804 disclose the combination of a calculator and a tape for determining brassiere sizes. The latter devices are not wholly satisfactory because each requires that the calculator be repositioned for each measurement.

SUMMARY OF THE INVENTION

It is an object of the invention to provide a new and improved brassiere sizer.

A further object of the invention is to provide a brassiere sizer which is easy to use and does not require repositioning to make all necessary measurements.

Another object of the invention is to provide a brassiere sizer which does not require expensive electronics or mechanical calculators.

These and other objects and advantages of the present invention will become more apparent from the detailed description thereof taken with the accompanying drawings.

In general terms, the invention comprises a brassiere sizer comprising of first member having a front face and a rear face, a first set of indicia on the first member and comprising length increments equally spaced apart and disposed in a circular array. A second member is mounted on the first member for rotation about a rotation axis concentric with the first set of indicia, and a second set of indicia on the second member is spaced apart in a circular array and denominating length increments and is disposed adjacent to the first set of indicia. A third set of indicia on one of the first and second members and comprising brassiere cup size indicia equally spaced apart and in an arcuate array concentric with the first set of indicia. An indicator is provided on the other of the first and second members and is positioned to be adjacent to the cup size indicia on the one of the first and second members. First and second measurement tapes are mounted for sliding movement on the first support. A connector is mounted on the rear face of the first member for mounting the first member on a brassiere band.

The length measurement indicia on the first member corresponding to the length increment on the first tape and the length measurement indicia on the second member corresponding to the length measurement indicia on the second tape, whereby when the length increment on the second member corresponding with the measurement around the torso of a brassiere along the lower brassiere band is aligned with the length indicia on the periphery of the first member corresponding with the measurement made by the second tape around the torso of the wearer and across the breasts, the indicator will indicate the breast cup size in the third indicia.

BRIEF DESCRIPTION OF THE DRAWINGS

FIG. 2 is a front elevational view of the brassiere sizer shown in FIG. 1;

FIG. 3 is a top view of the brassiere sizer shown in FIG. 1;

FIG. 5 is a rear view of the brassiere sizer of FIG. 1.

DETAILED DESCRIPTION OF THE PREFERRED EMBODIMENT

Figure 1:
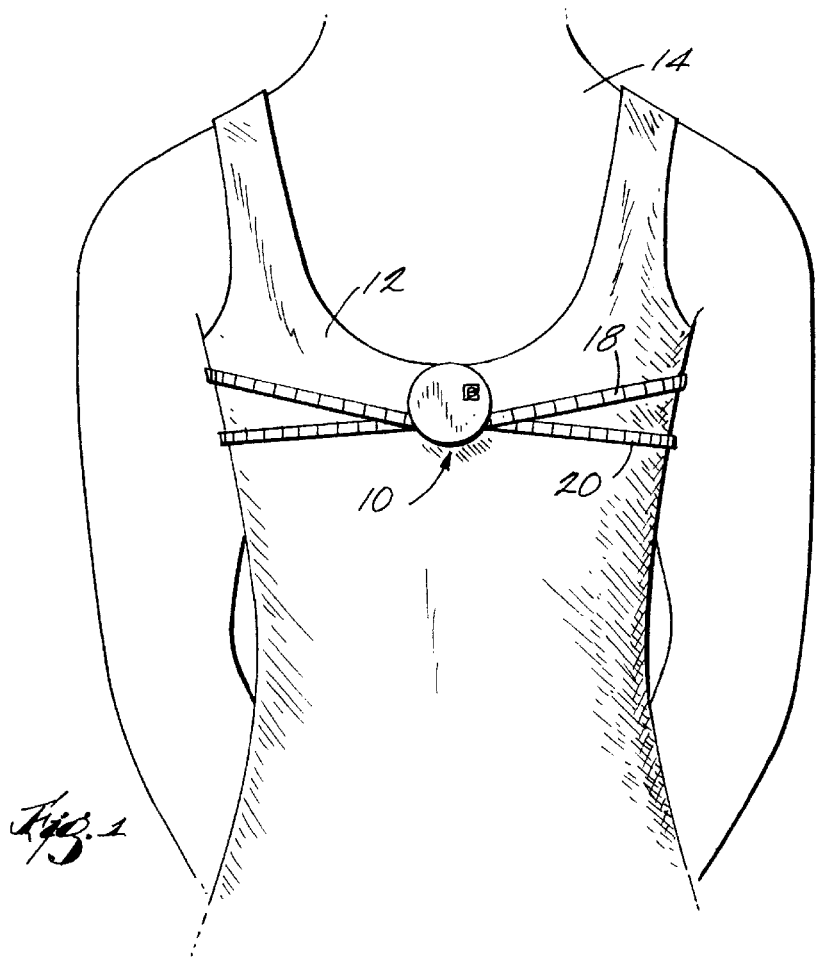
FIG. 1 shows the brassiere sizer according to the invention in its manner of use.
Figure 4:
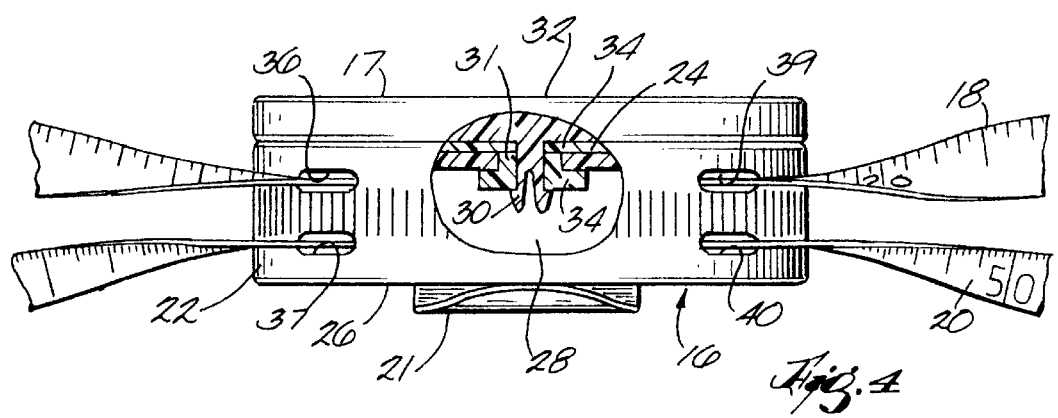
FIG. 4 is a side view of the brassiere sizer of FIG. 1 with parts broken away.

The brassiere sizer 10 according to the invention is shown in FIG. 1 mounted on the brassiere back band 12 of the user 14. The brassiere sizer 10 is shown in FIGS. 2–5 to include a first member 16, a second member 17 rotatably mounted on the first member 16, a pair of measuring tapes 18 and 20 and a connector 21. The first and second members may be formed of any suitable material, such as plastic.

In the preferred embodiment, the first member 16 comprises a housing having an annular sidewall 22, and circular front and rear walls 24 and 26, respectively, which are attached to the side wall 22 to define an enclosure 28. The second member 17 preferably comprises a circular dial having approximately the same diameter as the front wall 24 and includes an integral stem 30 extending from its rear surface and through a bearing member 31 positioned in a central hole 32 in front wall 24. A flange 34 on the bearing 31 slidably engages the inner surface of front wall 24 to stabilize the dial 17 during rotation and to retain the stem 30. The connector 21 preferably comprises a clip attached to the rear wall 26. The clip may be of any suitable material such as metal or plastic.

Measuring tapes 18 and 20 each include inch marks. For example, the first tape 18 may include inch marks 2"–60" and the second tape may include inch marks 5"–60". While all of the indicia are denominated in inches, it will be appreciated that metric indicia may alternately be used.

Two pair of parallel slots, 36, 37 and 39, 40 are formed in the side wall 22 and are spaced apart adjacent to a lower portion thereof. The slots 36, 39 slidably support tape 18 and slots 37, 40 slidably support tape 20. Specifically, tape 18 extends through slots 36 and 39 and tape 20 extends through slots 37 and 40.

There is a first set of indicia 42 on the outer surface of the side wall 22 and representing breast measurements made with tape 18. The first set of indicia 42 represent inches and are denominated, for example, 32"–48".

The front face of dial 17 includes a second set of indicia 44 spaced apart adjacent its periphery and representing the band circumference measurements made with tape 20. In the illustrated embodiment, the measurement indicia 44 represent, for example, inches 30"–44". The spacing between the second set of indicia 44 on the dial 17 are the same as those of the first set of indicia 42 on the side wall 22.

The front wall 24 has a plurality of cup size indicia AA, A, B, C, D and DD applied in any suitable manner and arranged in an arc which is concentric with the side wall 22. There is also a window 43 formed in dial 17 and sized to expose one of the cup size indicia at a time. In the illustrated embodiment, the B cup size indicia is shown to be exposed through window 43 while the remainder of the cup size indicia are covered. It will be appreciated that when the dial 17 is rotated, one of the other cup size indicia will be exposed depending on the angle of rotation. While in the preferred embodiment the cup size indicia are on the housing 16 and the window or indicator is on the dial 17, the invention contemplates a reversal where the cup size indicia are on the dial and an indicator, such as a pointer, is on the housing.

In operation, the housing 16 is clipped to the brassiere back band 12. The tape 20, which begins at the 5" mark, is used to measure the brassiere band circumference below the breast cups. This provides the band size which is equal to the length in inches plus five. For this reason, the tape 20 starts at 5". Without moving the housing 16, the tape 18 is then used to measure about the individual's torso and across the breast cups. This provides the breast cup measurement. The brassiere sizer 10 may then be removed and the dial 17 rotated until the band measurement on its front face is aligned with the breast cup measurement on the surface of the side wall 22. As indicated, the band measurement is made with tape 20 and the breast cup measurement is made with tape 18. When the dial 17 is rotated so that the band measurement is aligned with the breast cup measurement on the housing 16, the window 43 exposes the correct cup size. In order to minimize errors, the tapes 18 and 20 may be color coded with the indicia 42 and 44. For example, the band tape 20 and the band indicia 44 may be a first color, such as blue, and the breast cup tape 18 and the breast cup indicia 42 a second color, such as red. Alternatively, a single tape can be used for the band measurment and the breast cup measurement.

The brassiere sizer according to the invention is simple and easy to use because it does not require repositioning the housing 16 in order to make the required measurements. Moreover, the brassiere sizer 10 calculates the correct cup size without complicated electronic or mechanical calculating devices.

While only a single embodiment of the invention has been illustrated and described, it is not intended to be limited thereby but only by the scope of the appended claims.

I claim:

1. A brassiere sizer comprising:
   a first member having first and second sides, a first set of indicia on the first member and comprising length increments equally spaced apart and disposed in a circular array,
   a connector mounted on one side of the first member for mounting the first member on a brassiere band,
   a second member mounted on the first member for rotation about a rotation axis concentric with the first set of indicia, a second set of indicia on the second member spaced apart in a circular array and comprising length increments and disposed adjacent to the first set of indicia,
   a third set of indicia on one of the first and second members and comprising brassiere cup size indicia equally spaced apart and in an arcuate array concentric with the first set of indicia,
   an indicator provided on the other of the first and second members and positioned to be adjacent to the cup size indicia on the one of the first and second members,
   first and second measurement tapes mounted on the first member for sliding movement relative thereto, and each including length increment indicia,
   the length measurement indicia on the first member corresponding to the length increment indicia on the first tape and the length measurement indicia on the second member corresponding to the length increment indicia on the second tape,
   whereby when the length increment indicia on the second member corresponding with the measurement around the torso of a person wearing a brassiere along the lower brassiere band is aligned with the length increment indicia on the periphery of the first member corresponding with the measurement made by the second tape around the torso of the person and across the person's breasts, the indicator indicates the breast cup size in the third indicia.

2. The brassiere sizer set forth in claim 1 wherein said third set of indicia is on the front face of the first member and the indicator is on said second member.

3. The brassiere sizer set forth in claim 1 wherein said first member comprises a housing having a front face and a rear face, said housing having a generally annular sidewall, the first indicia being disposed on the sidewall of the housing, said third indicia being on the front face of said housing, said second member comprising a dial rotatably mounted on the front face of said housing, said second indicia being disposed on the outer periphery of the second member.

4. The brassiere sizer set forth in claim 3 wherein said indicator comprises a window on the dial and spaced from the rotational axis of the dial a distance equal to the radius of the arc formed by the second indicia so that one of the third indicia will appear in said window for various rotational positions of the dial.

5. The brassiere sizer set forth in claim 4 and including a pair of openings spaced apart in the sidewall of the housing for slidably supporting the first tape and a second pair of spaced apart openings in the housing for slidably supporting the second tape.

6. The brassiere sizer set forth in claim 5 wherein said connector comprises a clip on the rear face of the housing.

7. The brassiere sizer set forth in claim 3 and including a pair of openings spaced apart in the sidewall of the housing for slidably supporting the first tape a second pair of spaced apart openings in the housing for slidably supporting the second tape.

8. The brassiere sizer set forth in claim 2 wherein said indicator comprises a window on the second member and spaced from the rotational axis of the second member a distance equal to the radius of the arc formed by the second indicia so that one of the third indicia will appear in said window for various rotational positions of the second member.

9. The brassiere sizer set forth in claim 1 wherein said connector comprises a clip on the rear face of the housing.

10. A brassiere sizer comprising:
    a first member having thereon a first set of indicia representing length increments disposed in an arcuate array;
    a connector mounted on said first member for mounting said sizer to a brassiere band;
    a second member mounted to said first member and having thereon a second set of indicia representing length increments disposed in an arcuate array adjacent to and concentric with said first set of indicia;
    a third set of indicia on one of said first and second members representing brassiere cup sizes and disposed in an arcuate array;
    a indicator provided on the other of said first and second members and positioned adjacent said third set of indicia; and
    a first and a second tape supported by one of said first and second members and including length increment indicia, said first tape adapted to measure the length around the torso of a person wearing a brassiere along the lower brassiere band, said second tape adapted to measure the length around the torso and across the breasts of a person wearing a brassiere;

whereby when the length increment from said first tape on said first set of indicia is aligned with the length increment from said second tape on said second set of indicia, said indicator aligns with said third set of indicia to indicate the breast cup size of the person.

11. The brassiere sizer of claim 10, wherein said second member is pivotally moveable relative to said first member.

12. The brassiere sizer of claim 10, wherein said first member is a housing and wherein said second member is a dial.

13. The brassiere sizer of claim 10, wherein said connector is a clip.

14. The brassiere sizer of claim 10, wherein said first and second tapes are slidably supported by said on first and second members.

* * * * *